US008267911B2

(12) United States Patent
Gallogly et al.

(10) Patent No.: US 8,267,911 B2
(45) Date of Patent: Sep. 18, 2012

(54) FLOW-THROUGH FLUID RESERVOIR

(75) Inventors: Dale Marvin Gallogly, Mount Vernon, OH (US); Charles R. Patzer, Columbus, OH (US); John C. Toomey, Carlsbad, CA (US)

(73) Assignee: Smiths Medical ASD, Inc., Rockland, MA (US)

( * ) Notice: Subject to any disclaimer, the term of this patent is extended or adjusted under 35 U.S.C. 154(b) by 987 days.

(21) Appl. No.: 11/760,089

(22) Filed: Jun. 8, 2007

(65) Prior Publication Data

US 2008/0306424 A1   Dec. 11, 2008

(51) Int. Cl.
*A61B 19/00* (2006.01)
(52) U.S. Cl. ........................................ 604/408; 604/403
(58) Field of Classification Search .................. 604/4.01, 604/6.09, 125, 127, 158, 164.01, 133, 181, 604/184, 186, 187, 188, 190, 195, 197, 218, 604/256, 403, 404, 405, 406, 407, 408, 533, 604/539; 600/573
See application file for complete search history.

(56) References Cited

U.S. PATENT DOCUMENTS

| | | | |
|---|---|---|---|
| 544,014 A | 8/1895 | Terramorse | |
| 554,614 A | 2/1896 | Beyer | |
| 3,050,059 A | 8/1962 | Wall et al. | |
| D203,730 S | 2/1966 | Coanda | |
| 3,253,592 A | 5/1966 | von Pechmann | |

(Continued)

FOREIGN PATENT DOCUMENTS

| | | | |
|---|---|---|---|
| EP | 0 575 917 B1 | 12/1993 | |
| EP | 1726867 A | 11/2006 | |
| EP | 1 316 289 A1 | 6/2007 | |
| NL | 0076771 | 11/1954 | |
| WO | 88/02638 | 4/1988 | |
| WO | 2005021069 A | 3/2005 | |

OTHER PUBLICATIONS

European Search Report and Preliminary Opinion issued in counterpart European Application No. EP 07 25 3302 issued Feb. 15, 2010 (6 pages).

(Continued)

*Primary Examiner* — Tatyana Zalukaeva
*Assistant Examiner* — Benedict L Hanrahan
(74) *Attorney, Agent, or Firm* — Wood, Herron & Evans, LLP (57) ABSTRACT

A flow-through fluid reservoir includes a body with a first fluid port, a member movable within the body by an actuator to increase or decrease a volume of a chamber defined by a sidewall of the body. The actuator has a second fluid port. Movable member has a fluid path therethrough such that fluid ports are in fluid communication irrespective of the position of the movable member or the volume of chamber. A shaped slot on the shell of the actuator and a projection on the body cooperate to constrain relative movement of the body and actuator along a path corresponding to the shaped slot. The slot advantageously may include a stop intermediate therealong. A canted aspect of the slot may be used to initiate relative movement of the member within body. The body includes an end wall through which the first fluid port communicates. A shroud is defined by a coaxial extension of the sidewall beyond the end wall to surround the first fluid port, and gripping elements may be provided on the shroud. The projection may include a vent communicating into a space between a flexible barrier and an internal wall of the body. The slot may also have a one-way opening with a cammed roof. A clip may be provided for mounting the reservoir and includes a support member supporting a clip member which releasably receives the shroud and supports a mounting member such as for a sample site.

37 Claims, 7 Drawing Sheets

U.S. PATENT DOCUMENTS

| | | | |
|---|---|---|---|
| 3,965,897 | A | 6/1976 | Lundquist |
| 4,373,535 | A | 2/1983 | Martell |
| 4,457,755 | A | 7/1984 | Wilson |
| 4,615,341 | A | 10/1986 | Marzolf et al. |
| D287,053 | S | 12/1986 | Bucchianeri et al. |
| 4,643,200 | A | 2/1987 | Jennings, Jr. |
| 4,673,386 | A | 6/1987 | Gordon |
| 4,685,910 | A | 8/1987 | Schweizer |
| 4,766,908 | A | 8/1988 | Clement |
| 4,772,273 | A * | 9/1988 | Alchas ............... 604/218 |
| 4,774,963 | A | 10/1988 | Ichikawa et al. |
| 4,781,702 | A | 11/1988 | Herrli |
| 4,838,855 | A | 6/1989 | Lynn |
| 4,936,315 | A | 6/1990 | Lineback |
| 5,090,962 | A | 2/1992 | Landry et al. |
| 5,095,914 | A | 3/1992 | Sarstedt |
| 5,135,489 | A | 8/1992 | Jepson et al. |
| 5,148,811 | A | 9/1992 | Messinger |
| 5,232,457 | A * | 8/1993 | Grim ............... 604/195 |
| 5,265,621 | A | 11/1993 | Simpson et al. |
| 5,324,266 | A * | 6/1994 | Ambrisco et al. ........ 604/125 |
| 5,522,804 | A | 6/1996 | Lynn |
| 5,540,557 | A | 7/1996 | Carson |
| 5,788,677 | A | 8/1998 | Botich et al. |
| D403,762 | S | 1/1999 | Gabbard et al. |
| 5,858,253 | A | 1/1999 | Holm |
| 5,891,105 | A | 4/1999 | Mahurkar |
| 5,938,637 | A | 8/1999 | Austin et al. |
| 5,976,112 | A | 11/1999 | Lyza, Jr. |
| 6,086,559 | A | 7/2000 | Enk |
| 6,086,568 | A | 7/2000 | Caizza |
| 6,224,561 | B1 | 5/2001 | Swendson et al. |
| 6,224,577 | B1 | 5/2001 | Dedola et al. |
| 6,254,576 | B1 | 7/2001 | Shekalim |
| D461,555 | S | 8/2002 | Binet et al. |
| 6,461,333 | B1 | 10/2002 | Frezza |
| 6,481,679 | B1 | 11/2002 | Bennett et al. |
| 6,585,700 | B1 | 7/2003 | Trocki et al. |
| 6,626,870 | B1 | 9/2003 | Yarborough et al. |
| 6,652,489 | B2 | 11/2003 | Trocki et al. |
| 6,716,187 | B1 | 4/2004 | Jorgensen et al. |
| 2003/0106917 | A1 | 6/2003 | Shetler et al. |
| 2003/0181825 | A1 | 9/2003 | Büttner |
| 2004/0049892 | A1 | 3/2004 | Messina |
| 2004/0133146 | A1 | 7/2004 | Broek et al. |
| 2005/0187532 | A1 | 8/2005 | Thurau et al. |
| 2006/0229571 | A1 * | 10/2006 | Peppel ............... 604/256 |
| 2006/0259006 | A1 | 11/2006 | McKay et al. |
| 2006/0284036 | A1 | 12/2006 | Aube |

OTHER PUBLICATIONS

Photograph of SECURE system, Images Processed Internally on Oct. 11, 2007.

Photograph of KIDS KIT system, Images Processed Internally on Oct. 11, 2007.

Photograph of VAMP system, Images Processed Internally on Oct. 11, 2007.

Photograph of VAMP PLUS system, Images Processed Internally on Oct. 11, 2007.

Photograph of SAFESET system, Images Processed Internally on Oct. 11, 2007.

European Search Report from counterpart European Application No. 07253114.8 (2 pages).

European Written Opinion from counterpart European Application No. 07253114.8 (3 pages).

* cited by examiner

FLOW-THROUGH FLUID RESERVOIR

FIELD OF THE INVENTION

The present invention relates to flow-through fluid reservoirs, and more particularly, to such fluid reservoirs as may be used in blood sampling systems.

DESCRIPTION OF PRIOR ART

Flow-through fluid reservoirs have been provided for a variety of medical purposes. One type of flow through reservoir looks like a typical syringe, having a tubular body or barrel with a fluid port at one end, a movable member that looks like a syringe piston in sealing engagement with the internal wall of the barrel and movable toward and away from the fluid port to vary the volume of the chamber between the member and the fluid port, and an actuator like a plunger coupled to the movable member for moving the member to vary the volume of the chamber. But unlike a syringe, the actuator also includes a fluid port and the movable member includes a fluid path therethrough coupled to the actuator fluid port. As a result, fluid may flow uninterrupted between the fluid ports irrespective of the volume of the chamber. This type of reservoir may be seen as an axial reservoir such that with tubing coupled to the ports fluid flows through the tubing and uninterrupted between the ports and through the movable member fluid path, with the chamber volume varying by relative movement of the member axially along the fluid flow path.

One application for flow-through reservoirs is in a blood sampling system. In such a system, a source of fluid such as saline is coupled through tubing to a patient's circulatory system. The tubing may include in series in the line various components such as a flush valve, a pressure sensing component such as a transducer or a dome to communicate pressure to a transducer attached to the dome, and a sample site for accessing fluid in the tubing. A reservoir is coupled in-line with, or at an access location, along the tubing. Axial reservoirs would typically be in-line with the movable member fluid path in series with the fluid flow path such that the saline flows through the reservoir between the fluid ports and the movable member fluid path thereof. In the pressure monitoring mode of the system, which is the typical state, the movable member is situated at or near the body fluid port so as to define a minimum volume of the chamber. In that state, and with the tubing filled with saline and the flush valve in its drip state, the tubing and any fluid path through the reservoir defines a hydrostatic column with the pressure of the saline in the tubing corresponding to the patient's blood pressure.

To take a blood sample, the actuator is manipulated to pull the movable member away from the body fluid port thereby increasing the volume of the chamber. Most of that volume will be filled with saline in the tubing downstream of the reservoir as it backs up from the patient. As the saline backs up toward and into the reservoir, blood from the patient fills into the tubing and into the sample site. As blood enters the tubing, it may become diluted with saline present in that part of the tubing, so it is desirable to pull enough blood into the line that the blood in the sample site is whole blood, undiluted by any of the saline. Some of the diluted blood may also be pulled into the reservoir. The sample site is accessed, such as by a needle or a blunt cannula attached to a syringe or other fluid-collecting device. After the blood sample is taken, fluid is to again flow towards the patient. The actuator is manipulated to move the movable member back towards the body fluid port so as to allow or drive the blood remaining in the tubing and/or reservoir to flow back toward and into the patient. The flush valve may also be activated to increase flow with saline from the source of supply.

Manufacturers strive to improve the design, manufacturability, usability and performance of flow-through fluid reservoirs, and blood sampling systems using such reservoirs.

SUMMARY OF THE INVENTION

The present invention provides improvements to flow-through fluid reservoirs, including axial reservoirs. To that end, and in accordance with the principles of the present invention, a shaped slot is defined on the actuator (or the body) and a projection is defined on the body (or the actuator), with the projection cooperating with the shaped slot to constrain relative movement of the body and actuator to telescope along a path corresponding to the shaped slot. The slot and projection provide an easy mechanism for manipulating the member to vary the volume of the reservoir.

The actuator may include a shell telescopingly received over the body, with the slot formed through a sidewall of the shell. The shell provides a larger member for the user to grip for manipulation of the movable member. Yet, in the minimum volume state, the shell substantially overlaps the body so as not to appear to be bulky or oversized.

The slot may include a cammed roof access opening sized for the projection to be receivable therethrough and into the slot to facilitate assembly of the reservoir. The cammed roof limits the ability of the projection to come back out of the slot, however, such that the number of components and/or assembly steps necessary to make the fluid reservoir is minimized.

The body may be provided with a shroud extending outwardly of the body and surrounding at least part of the body fluid port. The shroud may include gripping elements to facilitate a user in grasping the shroud to help in manipulating the actuator. The shroud may also provide a column receivable in a generally C-shaped clip member of a mounting device. To that end, a mounting clip may be provided having a support member, a generally C-shaped clip member coupled to the support member, and a mounting member coupled to the clip member. Advantageously, the clip member is sized to removably received the shroud of the fluid reservoir, and the mounting member is adapted to removably receive a sample site of a blood sampling system of which the fluid reservoir may form a part. The clip may also include channels receiving the shroud gripping elements to hold the body against rotation during manipulation of the actuator.

In accordance with a further aspect of the present invention, more precise control over the volume of the chamber may be achieved. In that regard, as the volume of the reservoir chamber is increased, such as to pull blood into a sample site of a blood sampling system, it is helpful to know when enough blood has been pulled back into the tubing that the blood in the sample site may be considered as being whole blood. One prior approach marks the tubing with a visual indicator positioned such that when blood reaches the marking, it is expected that sufficient blood has backed up into the tubing that the sample site has whole blood. Another prior approach marks the reservoir with volume indicators, such that as the actuator is manipulated, the position of the movable member aligns with an indicator of the volume increase of the chamber. When the desired volume is reached, whether by blood appearing at the marker on the tubing and/or alignment of the movable member with the selected volume indicator, manipulation of the actuator is stopped and the blood sample taken. In accordance with this further aspect of the present invention, at least one discrete stop is defined at an intermediate position along the shaped slot. The stop is located to correspond to a predetermined volume of the chamber, such that as the actuator is manipulated to enlarge the volume, the actuator will have a natural stop at the predetermined volume. In a blood sampling system, that stop may advantageously be predetermined to correspond to whole blood in the sample site based on the volumetric aspects of the tubing between the patient and the sample site.

The stop may be defined by a discontinuity in the direction of the shaped slot. In one embodiment, the slot defines a stair-step shape, with the discontinuity being at the pedestal of the adjoining step(s). Alternatively or additionally, the stop may be defined by a detent defined in the shaped slot. For situations where more blood is to be drawn back into the tubing, the actuator may be manipulated beyond the stop to pull more fluid into the reservoir. Even then, the stop serves an advantage in that it reduces the tendency to overpull or too quickly move the movable member in relation to the elasticity of the patient's vessel.

In accordance with a yet further aspect of the present invention, the slot may include at least one end configured to facilitate initiation of movement of the movable member to increase the volume of the chamber. In that regard, stiction between the movable member and the internal wall of the body may make it difficult to reliably initiate movement from the minimum volume position in order to expand the volume of the chamber. To that end, in accordance with the principles of this yet further aspect of the present invention, one end of the slot, such as the end adjacent the projection in the minimum volume state, has an aspect canted off the main path of the slot. The canted aspect creates a path of both rotational and axial relative movement between the body and the actuator. Consequently, simple rotation between the body and the actuator impels the projection axially so as to initiate movement of the movable member away from the body fluid port in a direction to expand the volume of the chamber.

It is often typical to include a collapsible or flexible barrier, such as a sheath, between the movable member and the back end of the body so as to reduce the risk of contamination of the area of the internal wall that may be exposed to fluid as the volume of the chamber increases. In accordance with a further feature of the present invention, it may be desirable to vent the space between the barrier and the body, such as by forming a vent through the projection communicating into that space. As a result, the projection may advantageously provide the dual functions of cooperating with the slot and venting the space in the body, without the need for a separate vent. The vent may be provided with a venting plug and/or microbial filter to minimize the risk of airborne germs gaining entry to the space within the body.

By virtue of the foregoing, there are thus provided improvements to flow-through fluid reservoirs, including axial reservoirs. The various features of the present invention may be used collectively or separately as warranted or necessary. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the present invention.

DETAILED DESCRIPTION OF THE DRAWINGS

With reference to FIGS. 1 through 4, there is shown an exemplary embodiment of a flow-through fluid reservoir 10 constructed in accordance with the various principles of the present invention. Reservoir 10 includes a generally rigid clear plastic body 12, such as a tubular barrel similar to a syringe body. Body 12 has a sidewall 14 comprised of an internal wall 16 defining a chamber 18 and an outer wall 20. Sidewall 14 extends between a proximal opening 22 into chamber 18 and a distal end wall 24 supporting a first fluid port 26 in fluid communication with chamber 18. End wall 24 is rigid and advantageously concave and port 26 may be tapered.

In the embodiment of reservoir 10 shown herein, sidewall 14 also extends distally and coaxially beyond end wall 24 to define a shroud 28 which advantageously extends a distance generally equal to the length of port 26 so as to surround fluid port 26. Shroud 28 is thus generally tubular and has generally the same outer diameter as sidewall 14. Shroud 28 may also include one or more gripping elements 30, such as raised, sinuous ribs of outer wall 20 and which extend between distal end 32 of shroud 28 and end wall 24 and may as shown herein also extend proximally of end wall 24 to a stop ring 34 formed on outer wall 20. A plurality of annular grooves 36 may be formed in outer wall 20 along the length thereof between proximal end 22 and stop ring 34 (such as at 0.5 ml intervals).

A projection 40 extends from outer wall 20 of body 12 near proximal opening 22. In the embodiment shown herein, projection 40 is hollow and defines an aperture 42 therethough sized to snugly receive a venting plug 44 therein. Venting plug 44 has a stem 46 with venting grooves 48 to permit air to vent from within body 20 through aperture 42, and a cap 50 providing an umbrella over and beyond projection 40. Alternatively or additionally, an anti-microbial filter (not shown) may be used to close off aperture 42. Projection 40 need not be vented, however. An annular ledge 52 is formed adjacent proximal opening 22 and an annular lip 54 is at opening 22.

Figure 2:
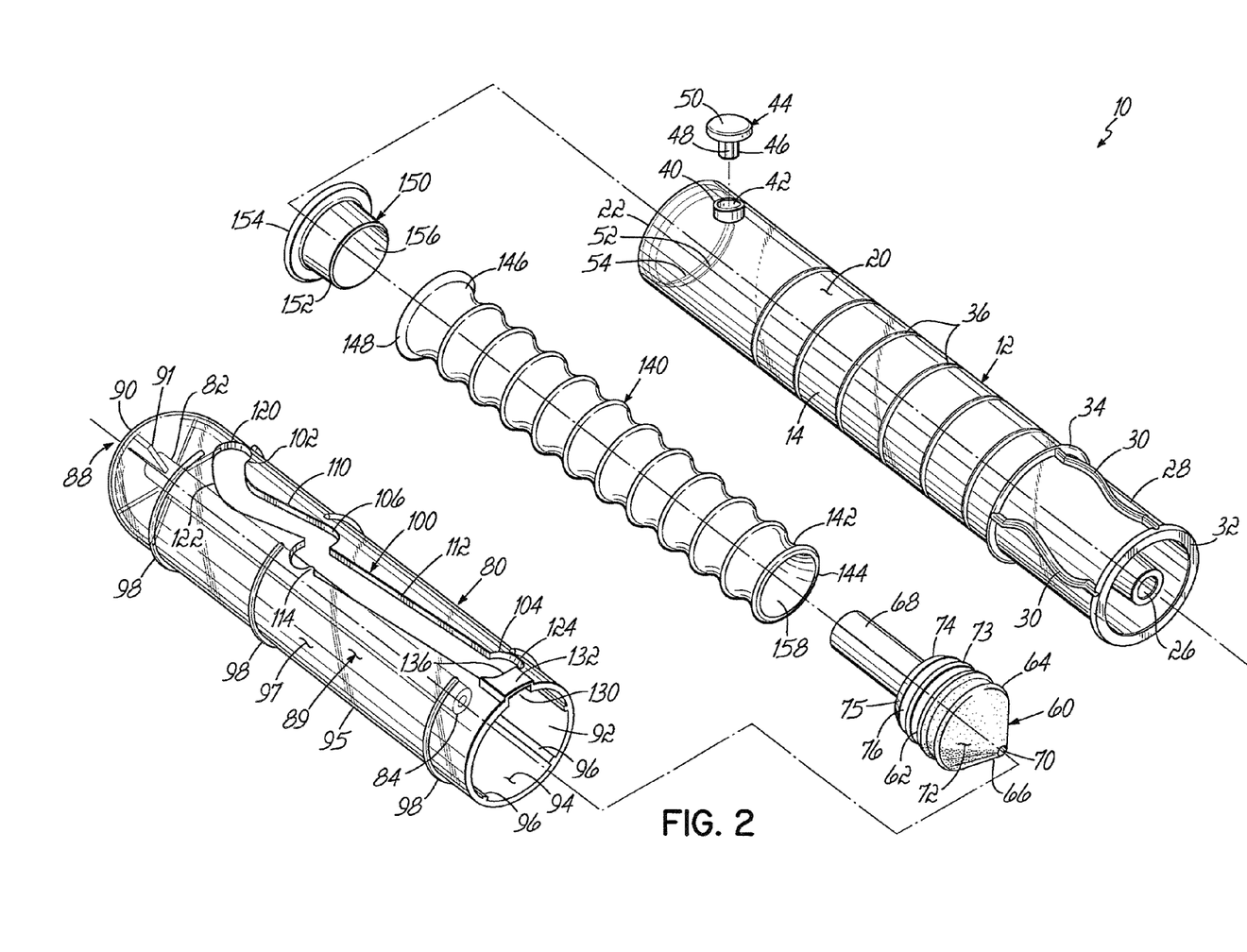
FIG. 2 is an exploded, perspective view of the components of the fluid reservoir of FIG. 1.
Figure 3A:
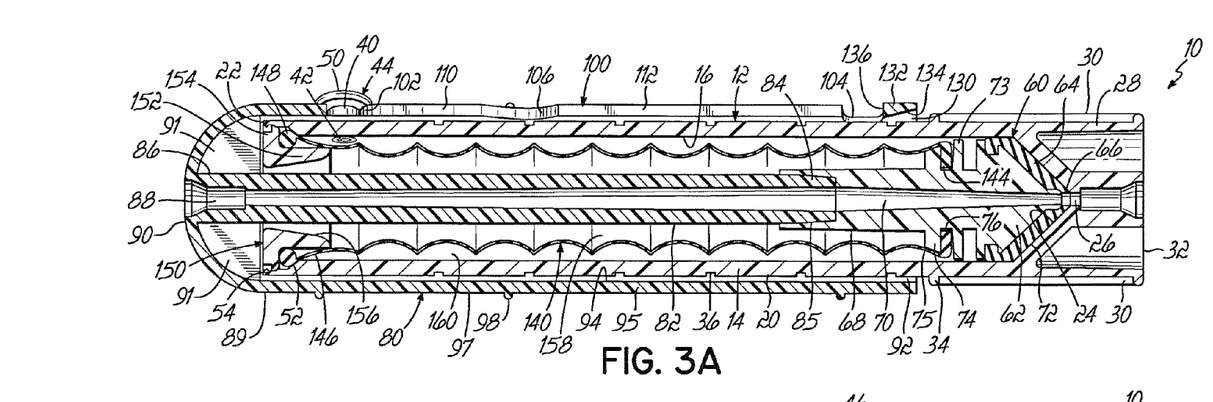
FIG. 3A is a cross-sectional view of the fluid reservoir of FIG. 1.
Figure 3B:
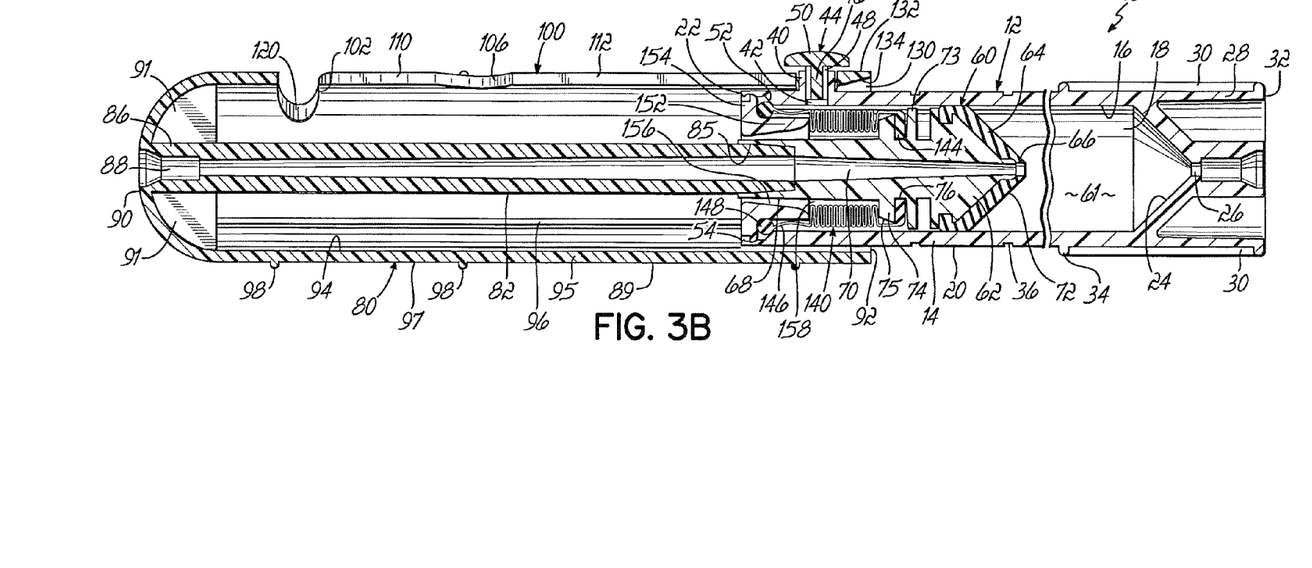
FIG. 3B is a cross-sectional view similar to FIG. 3A with the fluid reservoir at a maximum volume position.

Mounted within chamber 18 is a movable member 60 sized to sealingly engage internal wall 16 of body 20 between ledge 52 and end wall 24. Member 60 is movable within chamber 18 toward and away from distal end 32 and thus end wall 24 and first fluid port 26 to respectively decrease and increase the volume 61 of chamber 18. Movable member 60 in the embodiment shown herein includes a generally rigid clear plastic head 62 and an overmolded resilient, elastomeric cover 64. Cover 64 and/or internal wall 16 of body 12 may be lubricated with silicone oil. Head 62 includes a distal end 66 and a proximal stem 68. Head 62, cover 64 and stem 68 include a lumen 70 extending therethrough to define a fluid path through member 60. The distal end 66 is generally convex such that resilient cover 64 defines a distal, resilient surface 72 confronting and having a shape generally corresponding to the shape of end wall 24.

Mounted about stem 68 near head 64 is a first disc 73, and proximally thereof is a second disc 74 having a proximally cammed edge 75. Disc 73 is sized to correspond to the internal wall 16 of chamber 18 to help guide member 60 in its traverse of chamber 18. Disc 74 is smaller, and discs 73 and 74 are spaced apart to define an annular groove 76 therebetween for purposes to be described hereinafter. The fluid path 70 through member 60 is axially aligned with fluid port 26 such that even with surface 72 of movable member 60 bearing against end wall 24 (which defines a minimum volume of chamber 18 effectively at zero other than for the extent of fluid port 26 in the embodiment shown herein), fluid can flow between fluid path 70 and fluid port 26 without creating any appreciable dynamic effect on the fluid passing therethrough from the elastomeric material of cover 64.

Reservoir 10 also includes a generally rigid clear plastic actuator 80 including a hollow rod 82 having a distal end 84 coupled to enlarged port 85 of stem 68 and defining at its proximal end 86 a second fluid port 88, which may be tapered. With end 84 coupled to port 85, fluid may flow uninterrupted between ports 88 and 26, and through the fluid path 70 of movable member 60 irrespective of the position of member 60 or the volume of chamber 18. Actuator 80 in the embodiment shown herein includes an outer, tubular clear plastic shell 89 having a generally closed hemispherical proximal end 90 through which port 88 is accessed, and radial internal fins 91. Rod 82 is molded with end 90 and fins 91. Shell 89 also has an open distal mouth 92 sized to be telescopingly received over body 12. With rod 82 attached to stem 68, relative longitudinal movement between actuator 80 and body 12 causes movable member 60 to be moved toward and away from end wall 24. In the minimum volume position of member 60, distal mouth 92 of shell 89 is spaced adjacent to stop ring 34 such that shell 89 substantially encloses body 12 with the inner wall 94 of sidewall 95 of shell 89 being closely fitted about outer wall 20 of body 12. Longitudinally extending ribs 96 formed on inner wall 94 reduce wobble of body 12 within shell 89 as movable member 60 is moved to decrease and/or increase the volume 61 of chamber 18. Shell 89 may also include on its outer wall 97 of sidewall 95 a plurality of annular ribs 98.

Figure 1:
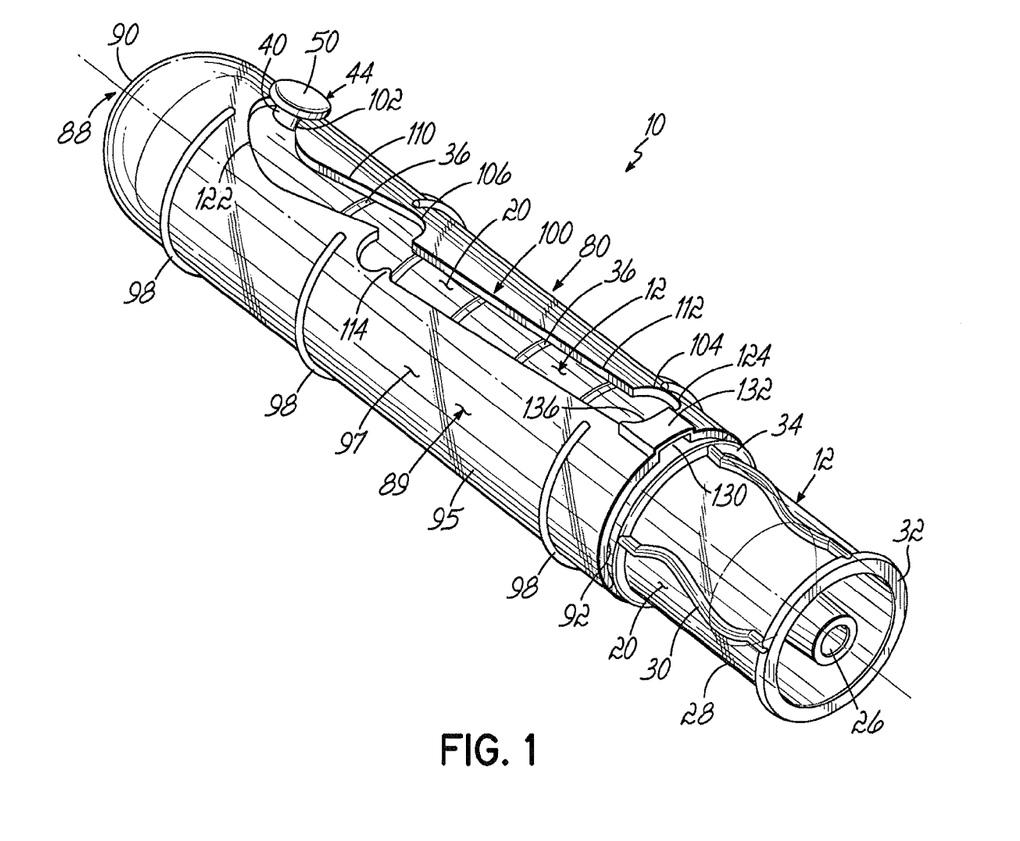
FIG. 1 is a perspective view of an exemplary embodiment of a flow-through fluid reservoir at a minimum volume position accordance with the principles of the present invention.
Figure 4:
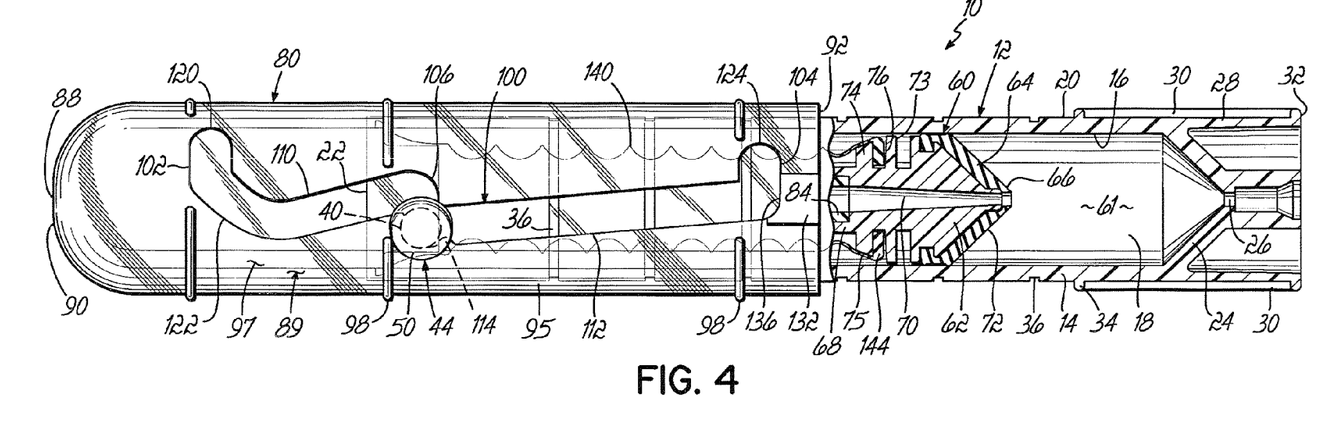
FIG. 4 is a side view, partially cut-away, of the fluid reservoir of FIG. 1 at a preselected volume position intermediate of the minimum and a maximum volume positions.

To facilitate relative movement between body 12 and actuator 80, shell 89 is provided with a generally longitudinally extending, shaped or contoured slot 100 extending through sidewall 95 of shell 89 and through which projection 40 is received. Slot 100 and projection 40 cooperate to constrain relative movement of body 12 and actuator 80 along a path corresponding to the shape of slot 100. Slot 100 has a proximal end 102 in which projection 40 resides in the minimum volume of chamber 18 (which may be 0 ml in the embodiment shown herein but could be greater than 0 ml in other embodiments), and a distal end 104 in which projection 40 resides in a maximum volume position of chamber 18 (which may be 13 ml in the embodiment shown herein). In order to control movement of member 60 to a predetermined volume 61 of chamber 18, such as 5 ml in the embodiment shown herein, slot 100 includes a discrete stop 106 intermediate of ends 102 and 104.

In the embodiment shown herein, shaped slot 100 has a first segment 110 extending between proximal end 102 and stop 106 and a second segment 112 extending between stop 106 and distal end 104. Each segment 110 and 112 extends generally longitudinally and circumferentially, but offset like stair-steps such that they meet up at a pedestal defining stop 106 as a discontinuity in the direction of the slot 100. Stop 106 may alternatively or additionally include a detent 114. As projection 40 traverses from proximal end 102 of slot 100 along segment 110, it will be impeded at stop 106 and will not generally continue in its traverse toward distal end 104 without relative rotation between the body 12 and actuator 80 to lift projection 40 into segment 112 and/or to overcome detent 114.

The proximal end 102 of slot 100 includes a parking portion 120 in which projection 40 is held until body 12 and actuator 80 are relatively rotated in a direction to bring projection 40 into segment 110. Parking position 120 advantageously extends generally transverse to the longitudinal extent of shell 89. Slot 100 also includes a canted portion 122 between parking portion 120 and segment 110 against which projection 40 bears to create an axially directed force to move projection 40 longitudinally as body 12 and actuator 80 are relatively rotated to bring projection 40 out of its parked position within parking portion 120 and to thus initiate movement of movable member away from end wall 24. Canted portion 122 extends longitudinally and circumferentially, the latter opposite to that of segment 110 such that parking portion 120 and canted portion 122 may be seen as defining a hook at proximal end 102. A second parking portion 124 may be provided at the distal end 104 of slot 100 to hold movable member 60 in the maximum volume position with projection 40 parked in portion 124. Stop 106 may also thus be viewed as an intermediate park position for projection 40. Also, while only one stop 106 is shown, depending upon the application, multiple discrete stops could be provided each corresponding to respective predetermined volumes 61 within chamber 18. Such further stops would also increase the number of slot segments, as desired.

Assembly typically might involve inserting proximal end opening 22 of body 12 into distal mouth 92 of shell 89 without venting plug 44 attached to projection 40 until after projection 40 passes into slot 100. To facilitate such assembly, slot 100 is provided with an access opening 130 at distal end 104. Opening 130 includes a roof 132 positioned such that its cammed underside 134 is beyond the outer diameter of outer wall 20 adjacent mouth 92 of shell 89, and decreases downwardly as it progresses proximally to back edge 136 at slot distal end 104 and which is at or close to that outer diameter. Projection 40 may thus be inserted into slot 100 through opening 130 by camming against roof 132 until it passes underside 134 and into projection 100, whereat the back edge 136 serves to minimize the ability of projection 40 from backing distally out of slot 100. Cap 50 of venting plug 44 is sized to be larger than slot 100 and/or opening 130 such that projection 40 is further held within slot 100 by attachment of venting plug 44 thereto after insertion of body 12 into shell 89.

Reservoir 10 also includes a flexible barrier member in the form of a ringed sheath 140. The distal end 142 of sheath 140 terminates in a ring 144 sized to be received over the cammed edge 75 of disc 74 and into the annular gap or groove 76 between discs 73, 74 whereat the distal end 142 is retained.

Proximal end 146 of sheath 140 has a radially outwardly extending lip 148 sized to fit on ledge 52 of body 12. A retaining cap 150 has a stem 152 sized to fit snugly within proximal end 146 of sheath 140 and an annular, stepped flange 154 sized to fit snugly within proximal opening 22 of body 12 against ledge 52 and under lip 54 so as to constrain lip 148 of sheath 140 thereat. Stem 152 and flange 154 have an aperture 156 therethrough to facilitate sliding passage therethrough of rod 82 of actuator 80 and to vent the space 158 within sheath 140. As best seen for example in FIG. 3A, a space 160 is defined between sheath 140 and internal wall 16 of body 12 which communicates through aperture 42 of projection 40 such that aperture 42 defines a vent. Sheath 140 collapses and expands in a generally accordion fashion as member 60 is moved towards and away from end wall 24.

In use, movable member 60 is typically in the minimum volume position with projection 40 in parking portion 120 as seen in FIG. 1. To expand volume 61 of chamber 18, body 12 and actuator 80 are manipulated by relative rotation therebetween, which drives projection 40 out of parking portion 120 and into canting portion 122 which initiates movement of member 60. Continued manipulation causes relative telescoping motion between body 12 and shell 89 along the path of slot segment 110 until projection 40 runs up against stop 106 corresponding to a predetermined volume 61 of chamber 18 as seen in FIG. 4. Further manipulation is required to move projection 40 out from stop 106 and into slot segment 112 for continued relative telescoping motion between body 12 and shell 89 along the path of slot segment 112 in order to further expand volume 61 of chamber 18, by moving projection 40 towards and into the distal parking portion 124 corresponding to a maximum volume position of chamber 18. The volume of chamber 18 may be decreased by reversing the foregoing movement(s). As the minimum volume is reached, confronting resilient surface 72 and rigid end wall 24 are shaped to sealingly engage one another in a direction radially inwardly from internal wall 16 along end wall 24 toward first fluid port 26 as member 60 is moved toward end wall 24 so as to define a shrinking volume 61 of chamber 18 in the direction toward fluid port 26 until surface 72 and end wall 24 are in substantially full engagement. To that end, end wall 24 and surface 72 may have an angular mismatch such as one degree. By way of example, end wall 24 may be angled at 45 degrees with surface 72 angled at 46 degrees. As a result, fluid (not shown) is forced from between movable member surface 72 and end wall 24 in a direction toward fluid port 26.

Figure 5:
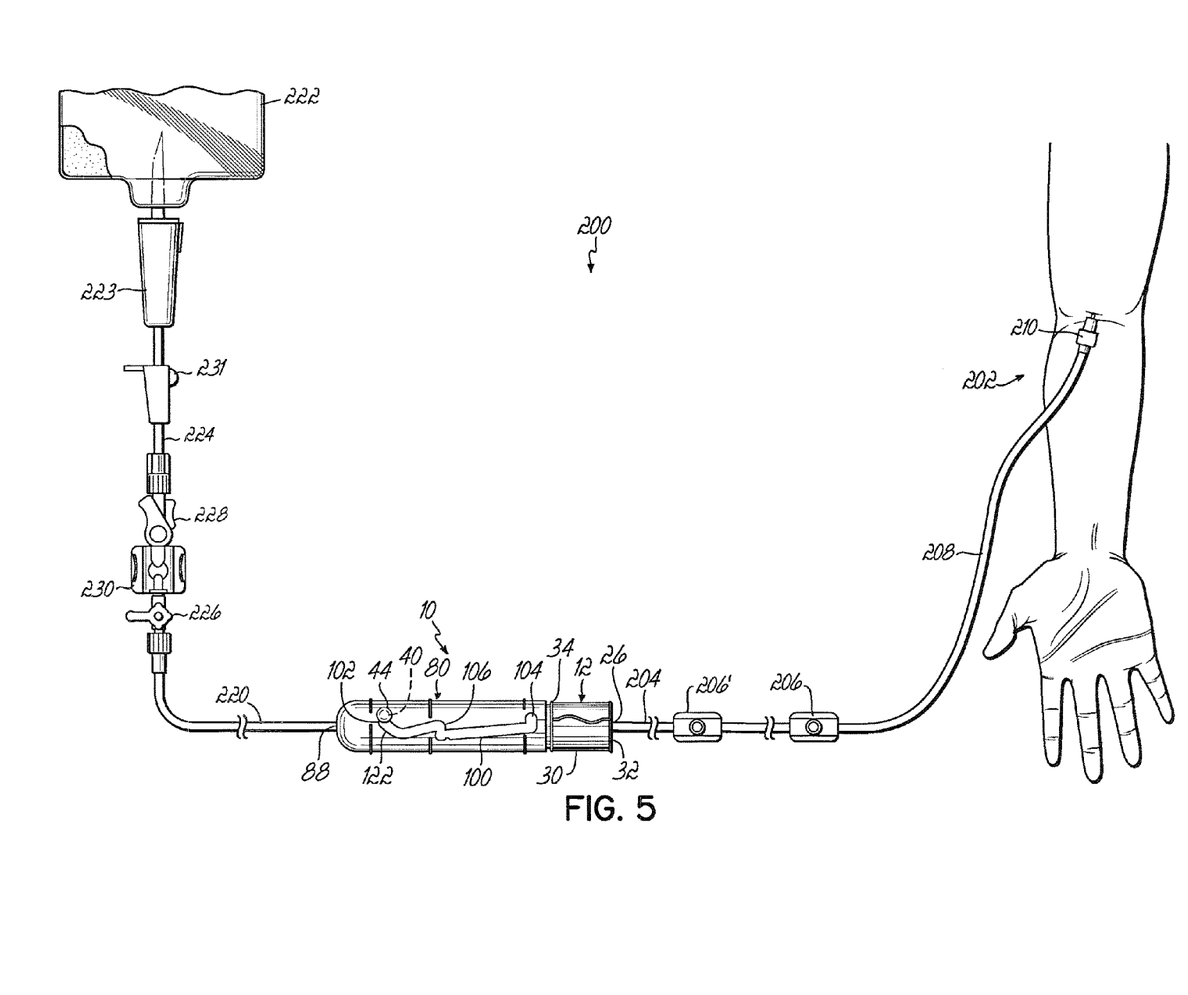
FIG. 5 is a schematic illustration of the fluid reservoir of FIG. 1 in a blood sampling system for purposes of explaining operation of the fluid reservoir in accordance with the principles of the present invention.

With reference to FIG. 5 there will be described use of reservoir 10 as part of a blood sampling system 200 for use with a patient 202. To that end, a first length of tubing 204 is operatively coupled to first fluid port 26 such as by being bonded within the taper thereof. A sample site 206 is coupled to tubing 204 and to the circulatory system of the patient 202, such as via further tubing 208 and a catheter 210. Sample site 206 may be of the type to be accessed via a needle (not shown) or more advantageously may be like that shown in copending U.S. patent application Ser. No. 11/687,533 filed Mar. 16, 2007 with a pre-slit septum to facilitate access with a blunt cannula. A second length of tubing 220 is operatively coupled to second fluid port 88 such as by being bonded within the taper thereof, and is adapted to be coupled to a source 222 of fluid such as saline via a spike 223 coupled to tubing 220 via further tubing 224, a zeroing stopcock 226, a flush device 228, and a pressure responsive element 230 which may be a pressure transducer or a disposable dome adapted to be coupled to a pressure transducer. A roller clamp 231 may be mounted to tubing 224. With clamp 231 open, flush device 228 normally allows a drip level of flow from source 222 through tubing 220, 204, 208, and element 230 such that the pressure therein corresponds to that of the patient's circulatory system. The zeroing stopcock 226 may be used during setup to clear the tubing of bubbles or air, and also to zero the transducer for calibration purposes, but otherwise need not be closed during use of system 200.

Reservoir 10 is normally in the minimum volume position with projection 40 in the parked position within parking portion 120 of slot 100 as shown in FIG. 5. In that position, blood pressure measurements are normally taken via element 230. When it is desired to take a blood sample, relative rotation is induced between body 12 and actuator 80, such as by securing shroud 28 against rotation and manipulating shell 89 with the hand to twist same and cause projection 40 to move against canting portion 122 of slot 100 whereby member 60 begins to move in a direction away from end wall 24 to thus increase the volume 61 of chamber 18. Continued manipulation of body 12 and shell 89 such as by pulling them axially apart causes body 12 and actuator 80 to move along the path defined by slot segment 110 to further increase volume 61 of chamber 18 until the stop 106 is reached, corresponding to a predetermined volume of fluid within chamber 18, such as the volume of fluid pull back at which it is expected that whole blood will be in sample site 206. Movement is stopped thereat and, if desired, projection 40 may be locked at stop 106 by manipulation of actuator 80, such as rotation of shell 89 relative to body 12, to move projection 40 along stop 106 and into detent 114 thereof. With projection 40 at stop 106, a blood sample may be taken as conventional.

A second sample site 206' may optionally be provided closer to reservoir 10 (i.e., further distal relative to the patient 202 than sample site 206). To facilitate taking a blood sample via site 206', the volume required for a blood sample is greater than the predetermined volume at stop 106. To that end, body 12 and actuator 80 may be further manipulated to move projection 40 out of and beyond stop 106 and along the path defined by slot segment 112 toward, and if desired all the way to, distal end 104 of slot 100 into parking portion 124 thereat to thus move member 60 further proximally and expand volume 61 of chamber 18 that much further. In that circumstance, impeding traverse of projection 40 at stop 106 has the added benefit of reducing the tendency to overpull or too quickly move the member 60 in relation to the elasticity of the vessel(s) of the patient's circulatory system. A stopcock (not shown) may be placed in-line between sample site 206 and catheter 210.

After taking the blood sample, manipulation of body 12 and actuator 80 is undertaken to move member 60 distally back along slot segment 112 (if that segment had been traversed to expand volume 61) and 110 towards, and ultimately into, the minimum volume position with surface 72 of cover 64 close to, if not engaging with, end wall 24. In the latter event, surface 72 and end wall 24 are angled such that there is a progressive squeezing closure thereof, from a radially outward location adjacent internal wall 16 toward port 26 as above described to flush from chamber 18 any blood (not shown) pulled into chamber 18 during expansion of volume 61 thereof.

Figures 6, 7, 8:
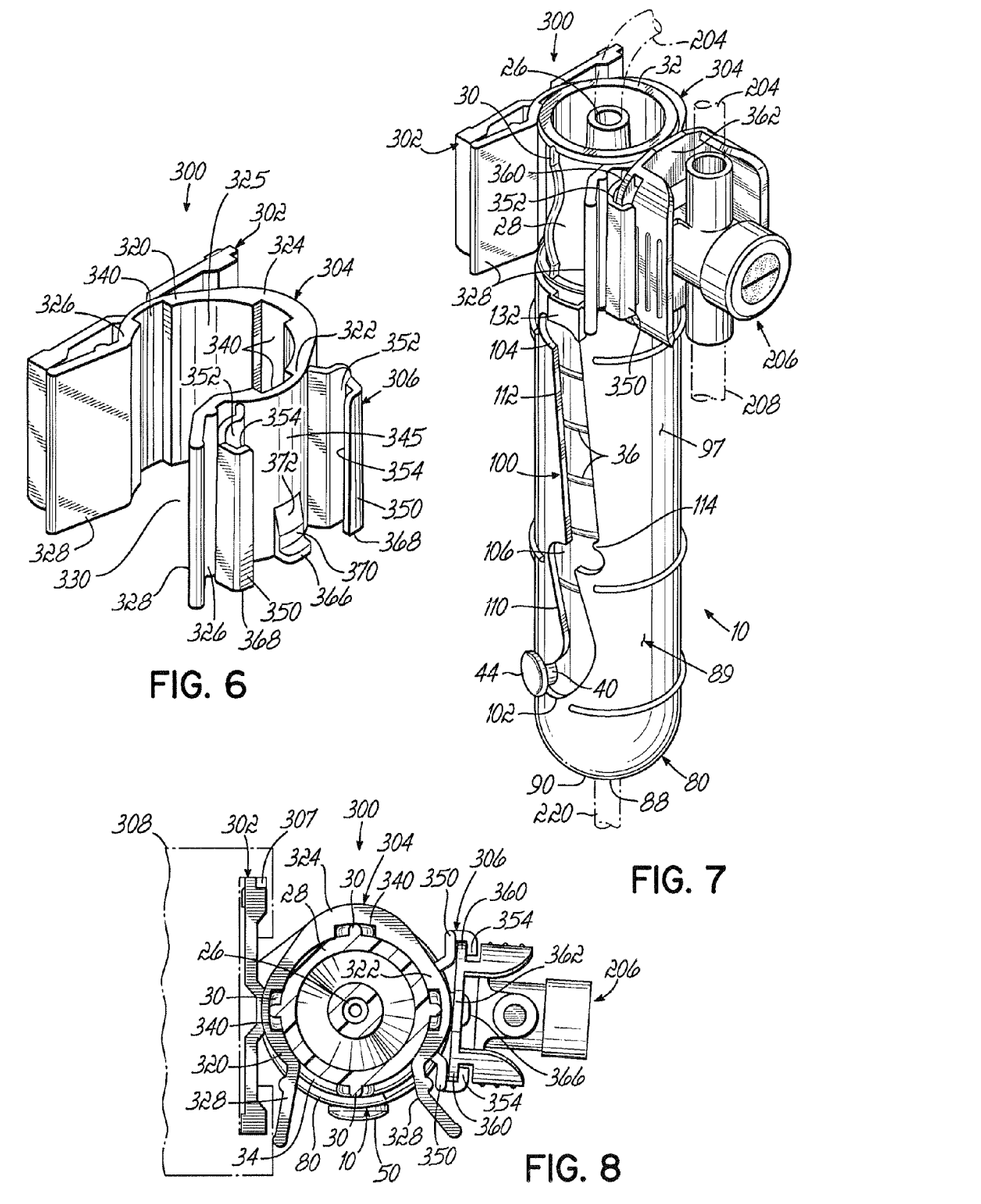
FIG. 6 is a perspective view of one embodiment of a mounting clip for use with the reservoir of FIG. 1 in a blood sampling system of FIG. 5.
FIG. 7 is a perspective view of the mounting clip of FIG. 6 with the fluid reservoir of FIG. 1 and a sample site of the blood sampling system of FIG. 5 mounted thereto.
FIG. 8 is a top view of the assembly of FIG. 7.
Figure 9:
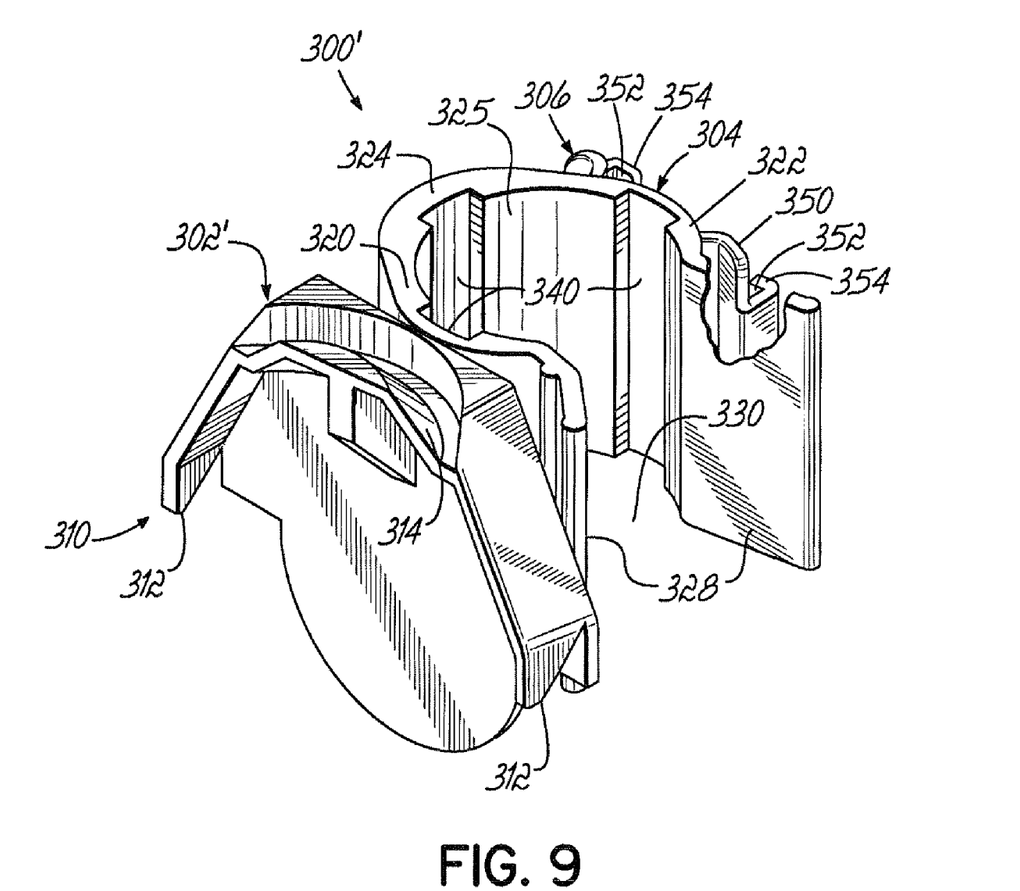
FIG. 9 is a perspective, partially cut-away view of a second embodiment of a mounting clip for use with the reservoir of FIG. 1 in the blood sampling system of FIG. 5.

Reservoir 10 is advantageously held in a vertical orientation with the first fluid port 26 aimed upwardly and with the sample site 206 readily accessible and mounted to a mounting pole or the like (not shown). To that end, a mounting clip 300 may be provided as seen in FIGS. 6 through 8. Clip 300 includes a support member 302, a generally C-shaped clip member 304 coupled to support member 302, and a mounting member 306 coupled to clip member 304. Support member 302 may define a generally vertical plate adapted to be slidably received within the channel-like mounting slot 307 of a transducer plate mounting bracket 308 (shown in phantom in FIG. 8) which in turn is held to a mounting pole (not shown). An example of a suitable mounting bracket is shown in U.S. Pat. No. 5,417,395. Support member 302 could also be defined by or include a generally horizontal ledge (not shown) by which to be secured directly to a pole clamp (also not shown). In another embodiment shown in FIG. 9, clip 300' includes clip member 304 and mounting member 306, but support member 302' has a plate-like appearance and a device coupler 310 having depending lower edges 312 and an upper arcuate groove 314 for mounting such as to a support coupler (not shown but an example of which is shown in U.S. Pat. No. 5,829,723). Clips 300 and 300' are otherwise the same and will be further described in relation to clip 300.

Clip member 304 includes a pair of arcuate arms 320, 322, with arm 320 coupled to support member 302 and arms 320, 322 merging in a yoke segment 324 to define a C-shaped interior 325 of clip member 304. The free end 326 of each arm 320, 322 defines a flared-out paddle 328 canted toward gap 330 between free ends 326 and through which shroud 28 of reservoir 10 may be inserted into gripping relation within the interior 325 of clip member 304. To that end, to mount reservoir 10 to clip 300, shroud 28 is pressed against paddles 328 which guide shroud 28 towards gap 330 and also urges paddles 328 somewhat apart to spread gap 330 to receive shroud 28 therethrough. When shroud 28 passes paddles 328, paddles 328 move towards one another whereat shroud 28 is securely gripped by arms 320, 322 of clip 300 as seen in FIGS. 7 and 8. To remove reservoir 10 from clip 300, shroud 28 may be pulled out through gap 330 and, if desired, paddles 28 may be urged apart by hand to facilitate such withdrawal.

One or more, or all, of arms 320, 322 and yoke segment 324 advantageously includes a generally vertically extending, recessed channel 340 therein confronting interior 325. Channels 340 are sized to snugly receive therein a respective gripping element 30 of shroud so as to resist rotation of body 12 when actuator 80 is manipulated. When reservoir 10 is mounted to clip 300 or clip 300', and the clip is secured to a mounting bracket (as at 308 shown in phantom in FIG. 8), manipulation of actuator 80 may be accomplished with one hand such as by grasping and rotation shell 89 near proximal end 90 thereof.

Mounting member 306 is coupled to arm 322 and is configured to removably receive a sample site 206 therein astride shroud 28, and thus port 26, of reservoir 10. To that end, mounting member 306 includes the outer aspect 345 of arm 322 extending between opposed receiver channels 350. Channels 350 have open tops 352 and open, confronting sides 354. Channels 350 are spaced apart so as to slidingly receive therein through top 352 the opposed edges 360 of a support plate 362 of sample site 206 by sliding plate 362 into channels 350 until plate 362 bottoms out against a stop rib 366 on arm 322 between channels 350 and aligned with the bottoms 368 thereof. Stop rib 366 may extend from a thickened portion 370 of arm 322 thereat which extends into the path of plate 362 so as to create a frictional engagement therewith to help hold site 206 in place in mounting member 306. Thickening portion 370 may include a cammed surface as at 372 to facilitate sliding plate 362 into that frictional engagement. Additionally or alternatively, bottoms 368 of channels 350 could be closed and provided with cammed surfaces (not shown) for that same purpose. Site 206 may be removed from mounting member 306 simply by sliding plate 362 up out of channels 350.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, while slot 100 has been shown as being on shell 89 of actuator 80, it could be on some other aspect of an actuator or could be associated with the body 12. In that regard, while projection 40 has been shown as being on body 12, it could alternatively be associated with actuator 80, such as shell 89 thereof. Also, while body 12 and shell 89 have been shown and described as being generally tubular, it will be recognized that various other shapes and configurations are possible. Similarly, while slot 100 has been shown as having a stair-step shape, other shapes or contours are also possible. Further, while lumen 70 of movable member 60 is shown as extending axially through stem 68, head 62 and cover 64, it will be appreciated that the lumen could communicate laterally through the side of head 62, in which event a distal aspect of head 62 and/or cover 64 will be sized smaller than the internal wall 16 so that fluid can flow therearound and over surface 72 to port 26. One or more standoffs (not shown) may be associated with surface 72 and/or end wall 24 to avoid closing off the flow path to port 26. Further alternatively, surface 72 and/or cover 64 could be rigid plastic, and may even be an integral part of head 62, rather than an overmolded element. Movable member 60 may include an O-ring or the like (not shown) for sealing engagement with internal wall 16. The invention in its broader aspects is therefore not limited to the specific details, representative apparatus and methods and illustrative examples shown and described. Accordingly, departures may be made from such details without departing from the scope or spirit of Applicant's general inventive concept.

Having described the invention, what is claimed is:

1. A flow-through fluid reservoir comprising:
a body having an internal wall defining a chamber and a first fluid port in fluid communication with the chamber;
a movable member sized to sealingly engage the internal wall and being movable within the chamber toward and away from the first fluid port so as to respectively decrease and increase a volume of the chamber, the movable member having a fluid path therethrough in fluid communication with the first fluid port;
an actuator operatively coupled in fixed spatial relationship to the movable member, the body and actuator being movable relative to each other in telescoping relationship so as to move the movable member toward and away from the first fluid port, the actuator having a second fluid port in fluid communication with the fluid path of the movable member, whereby fluid can flow between the first and second fluid ports;
a shaped slot defined on one of the body and the actuator; and
a projection defined on the other of the body and the actuator, the projection cooperating with the shaped slot to constrain relative movement of the body and the actuator along a path corresponding to the shaped slot.

2. The flow-through fluid reservoir of claim 1, the shaped slot including at least one discrete stop defined at an intermediate position along the shaped slot.

3. The fluid reservoir of claim 2, wherein the discrete stop includes a detent defined in the shaped slot.

4. The fluid reservoir of claim 2, wherein the shaped slot extends in a direction, the discrete stop being defined by at least one discontinuity in the direction of the shaped slot.

5. The fluid reservoir of claim 1 further comprising a flexible barrier coupled between the movable member and the body.

6. The fluid reservoir of claim 5 further comprising a vent formed through the projection and communicating with a space between the flexible barrier and the body.

7. The fluid reservoir of claim 6 further comprising a microbial filter associated with the vent.

8. The fluid reservoir of claim 6 further comprising a venting plug associated with the vent.

9. The fluid reservoir of claim 1 further comprising a cammed-roof access opening communicating with the slot, the access opening sized to receive the projection therethrough and into the slot.

10. The fluid reservoir of claim 1, the actuator including an elongated shell telescopingly received over the body.

11. The fluid reservoir of claim 10, wherein the shaped slot is on the actuator and the projection is on the body.

12. The fluid reservoir of claim 11 the shaped slot extending through a sidewall of the shell.

13. The fluid reservoir of claim 12 further comprising a flexible barrier coupled between the movable member and the body.

14. The fluid reservoir of claim 13 further comprising a vent formed through the projection and communicating with a space between the flexible barrier and the body.

15. The fluid reservoir of claim 14 further comprising a microbial filter associated with the vent.

16. The fluid reservoir of claim 14 further comprising a venting plug associated with the vent.

17. The fluid reservoir of claim 1, wherein the shaped slot has at least one end configured to facilitate initiation of movement of the movable member to increase the volume of the chamber.

18. The fluid reservoir of claim 1, wherein the shaped slot extends generally in a longitudinal direction of the body and has first and second ends, at least one of the first and second ends being canted with respect to portions of the shaped slot intermediate the first and second ends, whereby initiation of movement of the movable member from one of the first and second ends toward the other of the first and second ends is facilitated by twisting the actuator with respect to the body.

19. The fluid reservoir of claim 1, the body including a rigid end wall supporting the first fluid port and the movable member including a resilient surface confronting the end wall, the movable member being movable to bring the resilient surface into substantially full engagement with the end wall.

20. The fluid reservoir of claim 1, further comprising a shroud extending outwardly from the body and surrounding at least part of the first fluid port.

21. The fluid reservoir of claim 20, the shroud including gripping elements across a surface thereof.

22. The fluid reservoir of claim 1, wherein the body includes a shaped, rigid end wall and the movable member includes a shaped surface confronting the rigid end wall, the shapes of the end wall and the confronting surface adapted to sealingly engage one another in a direction toward the first fluid port as the movable member is moved toward the end wall so as to define a shrinking volume of the chamber in the direction toward the first fluid port, whereby to force fluid from between the movable member surface and the end wall in a direction toward the first fluid port.

23. The fluid reservoir of claim 1 further comprising a first length of tubing operatively coupled to the first fluid port of the body.

24. The fluid reservoir of claim 23 further comprising a sample site coupled to the first length of tubing.

25. The fluid reservoir of claim 23 further comprising a second length of tubing operatively coupled to the second fluid port of the actuator.

26. The fluid reservoir of claim 1 further comprising a second length of tubing operatively coupled to the second fluid port of the actuator.

27. A flow-through fluid reservoir comprising:
a body having an internal wall defining a chamber and a first fluid port in fluid communication with the chamber;
a movable member sized to sealingly engage the internal wall and being movable within the chamber toward and away from the first fluid port so as to respectively decrease and increase a volume of the chamber, the movable member having a fluid path therethrough in fluid communication with the first fluid port;
an actuator operatively coupled in fixed spatial relationship to the movable member, the body and actuator being movable relative to each other in telescoping relationship so as to move the movable member toward and away from the first fluid port, the actuator having a second fluid port in fluid communication with the fluid path of the movable member, whereby fluid can flow between the first and second fluid ports;
a projection defined on one of the body and the actuator; and
a slot defined on the other of the body and the actuator, the slot having a one-way access opening adapted to receive the projection therethrough and into the slot and to resist movement of the projection back out of the slot through the access opening.

28. The flow-through fluid reservoir of claim 27, the access opening including a cammed roof.

29. A flow-through fluid reservoir comprising:
a body having an internal wall defining a chamber and a first fluid port in fluid communication with the chamber;
a movable member sized to sealingly engage the internal wall and being movable within the chamber toward and away from the first fluid port so as to respectively decrease and increase a volume of the chamber, the movable member having a fluid path therethrough in fluid communication with the first fluid port;
an actuator operatively coupled in fixed spatial relationship to the movable member, the body and actuator being movable relative to each other in telescoping relationship so as to move the movable member toward and away from the first fluid port, the actuator having a second fluid port in fluid communication with the fluid path of the movable member, whereby fluid can flow between the first and second fluid ports;
a slot defined on one of the body and the actuator; and
a projection defined on the other of the body and the actuator, the projection cooperating with the slot for relative movement of the body and the actuator, the slot extending generally in a longitudinal direction of the body and having an aspect at one end of the slot being canted with respect to the longitudinal extent of the slot such that the projection bears against the canted aspect to facilitate initiation of movement of the movable member in response to relative rotation between the actuator with respect to the body.

30. A flow-through fluid reservoir comprising:
a body having an internal wall defining a chamber and a first fluid port in fluid communication with the chamber;
a movable member sized to sealingly engage the internal wall and being movable within the chamber toward and away from the first fluid port so as to respectively decrease and increase a volume of the chamber, the movable member having a fluid path therethrough in fluid communication with the first fluid port;

an actuator operatively coupled in fixed spatial relationship to the movable member, the body and actuator being movable relative to each other in telescoping relationship so as to move the movable member toward and away from the first fluid port, the actuator having a second fluid port in fluid communication with the fluid path of the movable member, whereby fluid can flow between the first and second fluid ports;

a slot defined on one of the body and the actuator;

a projection defined on the other of the body and the actuator, the projection cooperating with the slot for relative movement of the body and the actuator; and a flexible barrier coupled between the movable member and the body, the projection including a vent formed through the projection and communicating with a space between the flexible barrier and the body.

31. The flow-through fluid reservoir of claim 30 further comprising a venting plug associated with the vent.

32. The flow-through fluid reservoir of claim 31, the venting plug including a stem received in the vent and a cap extending over the vent.

33. The flow-through fluid reservoir of claim 30 further comprising a microbial filter associated with the vent.

34. A flow-through fluid reservoir comprising:

a generally tubular body having a sidewall and an end wall defining a chamber, and a first fluid port in fluid communication with the chamber through the end wall;

a movable member sized to sealingly engage the sidewall and being movable within the chamber toward and away from the end wall so as to respectively decrease and increase a volume of the chamber, the movable member having a fluid path therethrough in fluid communication with the first fluid port; and an actuator operatively coupled in fixed spatial relationship to the movable member, the body and actuator being movable relative to each other in telescoping relationship so as to move the movable member toward and away from the end wall, the actuator having a second fluid port in fluid communication with the fluid path of the movable member, whereby fluid can flow between the first and second fluid ports;

a slot defined on one of the body and the actuator;

a projection defined on the other of the body and the actuator, the projection cooperating with the slot for relative movement of the body and the actuator, the sidewall extending coaxially beyond the end wall to define a shroud surrounding the first fluid port.

35. The flow-through fluid reservoir of claim 34, the shroud extending beyond the end wall a distance substantially equal to a length of the first fluid port.

36. The flow-through fluid reservoir of claim 34, the shroud including at least one gripping element thereon.

37. The flow-through fluid reservoir of claim 36, the gripping element being a raised, sinuous rib.

* * * * *